_United States Patent_ [19]

Mishkin

[11] Patent Number: 5,902,336
[45] Date of Patent: May 11, 1999

[54] IMPLANTABLE DEVICE AND METHOD FOR REMOVING FLUIDS FROM THE BLOOD OF A PATIENT METHOD FOR IMPLANTING SUCH A DEVICE AND METHOD FOR TREATING A PATIENT EXPERIENCING RENAL FAILURE

[75] Inventor: Gary J. Mishkin, Chevy Chase, Md.

[73] Assignee: Mirimedical, Inc., Tamarac, Fla.

[21] Appl. No.: 08/732,852

[22] Filed: Oct. 15, 1996

[51] Int. Cl.$^6$ .................................. A61F 2/02; A61F 2/04; A61M 37/00; A61M 1/00
[52] U.S. Cl. ................................... 623/11; 623/12; 604/4; 604/5; 604/27; 604/28; 604/29
[58] Field of Search ........................... 623/11, 12; 604/4, 604/5, 6, 27, 28, 29, 274–278

[56] References Cited

U.S. PATENT DOCUMENTS

| | | | |
|---|---|---|---|
| 3,916,896 | 11/1975 | Ballard | 604/278 |
| 4,235,231 | 11/1980 | Schindler . | |
| 4,256,102 | 3/1981 | Monaco . | |
| 4,287,888 | 9/1981 | Schwarz | 604/278 |
| 4,338,190 | 7/1982 | Kraus . | |
| 4,354,933 | 10/1982 | Lester . | |
| 4,435,171 | 3/1984 | Goldberg . | |
| 4,490,137 | 12/1984 | Moukheibir | 604/29 |
| 4,518,497 | 5/1985 | Tsuda . | |
| 4,588,407 | 5/1986 | Isono et al. | 604/6 |
| 4,702,829 | 10/1987 | Polaschegg . | |

(List continued on next page.)

OTHER PUBLICATIONS

The Urologic Clinics of North America, Renal Vascular Disease and Transplantation, vol. 21, No. 2, May 1994, Andrew C. Novick, pp. 324,325,328,331,338.

Hemofiltration; 1986; M. J. Lysaght, The History of Hemofiltration, pp. 2–15.

Hemofiltration; 1986; L. W. Henderson, The Future of Hemofiltration, pp. 309–315.

Trans Am Soc Artif Intern Organs, 1980, vol. XXVI, Continuous Ambulatory Hemofiltration, S. Shaldon et al., pp. 210–212.

Trans Am Soc Artif Intern Organs, 1986, vol. XXXII, Continuous Arterio–venous Hemofiltration in a Wearable Device to Treat End–Stage Renal Disease, A. Murisasco et al., pp. 567–571.

Arterio–venose Hamofiltration, Nieren–(Ersatz)–Therapie im Intensivpflegebereich, 1982, Peter Kramer, Intestinale Substitution bei arterio–venoser Hamofiltration.

(List continued on next page.)

_Primary Examiner_—Michael J. Milano
_Assistant Examiner_—Tram A. Nguyen
_Attorney, Agent, or Firm_—Pillsbury Madison & Sutro

[57] ABSTRACT

An implantable ultrafiltration device for removing low to medium molecular weight solutes and fluids from the blood of a patient experiencing renal failure, the device including: a pump having an inlet and an outlet; a first component for forming a first fluid flow path between the patient's vascular system and the pump inlet; a filter interposed in the first fluid flow path, the filter being permeable to water and substantially impermeable to blood cells and proteins; and a second component for forming a second fluid flow path between the pump outlet and the patient's bladder, wherein the pump, the first and second components, and the filter are all constructed to be surgically implanted in the patient's body. For removing unwanted fluids from the blood of a patient experiencing renal failure the first component is connected in the vascular system of the patient and the second component is implanted in the patient's bladder or ureter; and the pump is then operated to cause fluid to flow through the filter at a controlled rate in order to maintain the volume of the blood in the vascular system and total body volume at a selected value. The infusion of peritoneal solution free of osmotic agents can also be carried out in conjunction with conventional hemodialysis or with operation of the implanted device.

20 Claims, 2 Drawing Sheets

U.S. PATENT DOCUMENTS

| | | |
|---|---|---|
| 4,708,802 | 11/1987 | Rath . |
| 4,765,907 | 8/1988 | Scott . |
| 4,817,600 | 4/1989 | Herms . |
| 4,861,485 | 8/1989 | Fecondini . |
| 4,976,683 | 12/1990 | Gauthier et al. .......................... 604/28 |
| 5,011,607 | 4/1991 | Shinzato . |
| 5,037,385 | 8/1991 | O'Byrne . |
| 5,092,886 | 3/1992 | Dobos-Hardy . |
| 5,100,419 | 3/1992 | Ehlers ..................................... 606/140 |
| 5,336,165 | 8/1994 | Twardowski ............................. 623/12 |
| 5,391,143 | 2/1995 | Kensey ..................................... 604/28 |
| 5,397,354 | 3/1995 | Wilk et al. ............................... 623/11 |
| 5,484,424 | 1/1996 | Cottenceau . |
| 5,549,674 | 8/1996 | Humes et al. ............................ 623/12 |

OTHER PUBLICATIONS

ASAIO Journal, 1992, Slide Forum 4, Hemodialysis/Blood Volume and Flow, Continuous Measurement of Blood Volume During Hemodialysis by an Optical Method, Jean–Paul P. M. De Vries et al., pp. M181–M185.

Journal of the American Society of Nephrology, vol. 6, No. 2, 1995, Determination of Circulating Blood Volume by Continuously Monitoring Hematocrit During Hemodialysis, John K. Leypoldt et al., pp. 214–219.

The International Journal of Artificial Organs, vol. 18, No. 9, 1995, Hemoscan: A Dialysis Machine–Integrated Blood Volume Monitor, F. Paolini et al., pp. 487–494.

Kidney International, vol. 44 (1993), Non–Invasive Monitoring of Blood Volume During Hemodialysis: Its Relation with Post–Dialytic Dry Weight, Jean–Paul P. M. De Vries et al., pp. 851–854.

Kidney International, vol. 49 (1996), A Device and a Method for Rapid and Accurate Measurement of Access Recirculation During Hemodialysis, Robert M. Lindsay et al., pp. 1152–1160.

ASAIO Journal, 1995, vol. 41, Determination of Fluid Shifts During Chronic Hemodialysis Using Bioimpedance Spectroscopy and an In–Line Hematocrit Monitor, Amer E. Jabara et al., pp. M682–M687.

Transonic Systems, Inc., Access Flow, Access Recirculation, Cardiac Output Measurements During Hemodialysis, Oct. 1994, Nikotai Krivitski et al.

MicroMo Motors, DC MicroMotors Series 1212 specification sheet

MiniMed 506: Simple, Safe, Smart, Jul. 8, 1996, Internet web page.

The MiniMed 506 Insulin Pump, Jul. 8, 1996, Internet web page.

The MiniMed 2001 Implantable Insulin Pump, Jul. 8, 1996, Internet web page.

Fig. 4

IMPLANTABLE DEVICE AND METHOD FOR REMOVING FLUIDS FROM THE BLOOD OF A PATIENT METHOD FOR IMPLANTING SUCH A DEVICE AND METHOD FOR TREATING A PATIENT EXPERIENCING RENAL FAILURE

BACKGROUND OF THE INVENTION

The present invention relates to devices and methods for treating patients suffering from renal diseases.

The leading causes of death in patients with End Stage Renal Disease (ESRD) are cardiac related. Cardiac related diseases include acute myocardial infarction, cardiac arrest, cardiac arrhythmia, cardiomyopathy, atherosclerotic heart disease, valvular, pericarditis, and pulmonary edema. These diseases account for 43% of all deaths in this population or roughly 17,000 deaths per year (United States Renal Data System, USRDS).

ESRD patients have a high prevalence of cardiac disease due to their inability to excrete fluids. In individuals with normal renal function, the blood is filtered and toxins and fluids are removed as necessary. Since ESRD patients are not capable of sufficiently excreting fluids, water and other fluids which are consumed remain in the body until they are removed by ultrafiltration (removal of excess fluid from the body) during dialysis.

The body's fluid retention mechanism tends to be consistent from patient to patient. The blood volume is usually first to expand. The blood volume is known to increase in size by as much as 20%. This places undue stress on the heart and the circulatory system as is evident by the rise in blood pressure and concurrent incidence of heart failure in ESRD patients. When the extracorporeal system is at its maximum fluid capacity (related to oncotic and osmotic forces), the fluid then distributes throughout the body, usually ending up in the extremities such as ankles, hands and other tissues as edema. The total quantity of fluid which the body can hold varies from patient to patient, however volumes as large as 7 liters, or 15 pounds, of fluid are common. The result of this fluid overload is reflected in increased hypertension and edema. If the body continues to take on more fluid, the fluid then enters the pleural cavities and the patient has shortness of breath. Oxygen uptake in the lungs is reduced as air in the alveoli becomes displaced by water. If this condition is not treated, death can result. The treatment currently employed is ultrafiltration.

Once the fluid is removed and the proper dry weight of the patient is reached, blood pressure will drop and breathing will return to normal. However, repeated increases and decreases in blood volume are believed to inflict damage to the heart and vascular system, thereby increasing the risk of cardiac disease.

SUMMARY OF THE INVENTION

It is a primary object of the present invention to remedy the above-described shortcomings of existing ultrafiltration procedures by effecting a continuous removal of excess fluid from the circulatory system on an ambulatory basis.

A more specific object of the invention is to provide a simple and reliable implantable device which can continuously remove excess fluid from the circulatory system of a renal disease patient in a controlled manner.

The above and other objects are achieved, according to the invention, by an implantable ultrafiltration device for removing low to middle molecular weight solutes and fluids from the blood of a patient experiencing renal failure, the device comprising: a pump having an inlet, an outlet and means for impelling fluid from the inlet to the outlet; first means for forming a first fluid flow path between the patient's vascular system and the pump inlet; a filter interposed in the first fluid flow path, the filter being permeable to water and substantially impermeable to blood cells and protein; and second means for forming a second fluid flow path between the pump outlet and the patient's bladder, wherein the pump, the first means, the second means and the filter are all constructed to be surgically implanted in the patient's body.

The invention further provides a method for removing unwanted fluids from the blood of a patient experiencing renal failure by implanting the device described above by connecting the first means in the vascular system of the patient and implanting the second means in the patient's bladder or ureter; and operating the pump to cause fluid to pass through the filter at a controlled rate in order to maintain the volume of the blood in the vascular system and the total body volume at a selected value.

Devices and procedures according to the present invention will eliminate fluid overload, thereby eliminating the complications associated with fluid overload, will help reduce the incidence of cardiac disease, lower blood pressure and reduce the incidence of pulmonary edema, and will permit patients to consume fluids as needed and wanted without the constant concern of monitoring fluid intakes. This will lead to improved patient health, improved quality of life and improvements in patient morbidity and mortality. These improvements are achieved by slowly removing excess water and low to middle molecular weight solutes which build up in ESRD patients between dialysis sessions.

A device according to the invention will have, in addition to the components described above, a telemetry and control system which includes telemetry components that allow physiological conditions of the patient and the operating state of the device, as measured by sensors, to be communicated to care providers, as well as control components for controlling operation of the device in response to signals provided by certain sensors. An electro-optical or conductivity sensor can be provided to detect changes in blood volume and the resulting measurement can then be used in a feedback loop to prevent excessive fluid removal and to achieve and maintain euvolemia. The constant fluid removal achieved by this device will reduce treatment times of dialysis, reduce blood pressure, reduce edema, reduce the incidence of heart failure among ESRD patients and improve the quality of life.

The invention also includes a method of treating a patient experiencing renal failure, comprising infusing a quantity of a peritoneal solution which is substantially free of osmotic agents into the peritoneal cavity of the patient, and allowing the solution to be absorbed into the patient's blood and removing absorbed fluid by a means for filtration.

DESCRIPTION OF THE PREFERRED EMBODIMENTS

Figure 1:
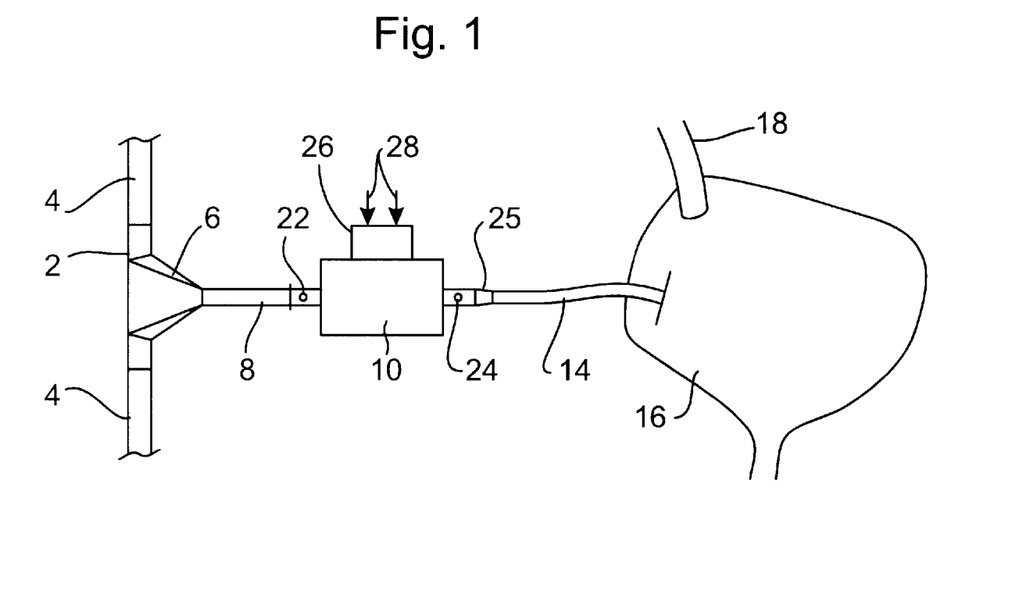
FIG. 1 is a simplified pictorial view of a device according to the invention implanted in the pelvic region of a patient.

The embodiment shown in FIG. 1 is composed of a first means for forming a fluid flow path from the patient's vascular system, this first means being composed essentially of a tubular graft 2 inserted between two portions 4 of an artery and/or vein, a funnel-shaped fluid guide member 6 and a first conduit 8. This embodiment of the device further includes a pump 10 having an inlet connected to the outlet end of conduit 8 and an outlet connected to the inlet end of a further conduit 14 which constitutes a second means for forming a second fluid flow path from the pump outlet. In this embodiment, the outlet end of second conduit 14 is surgically implanted in the patient's bladder 16. Alternatively, the outlet end of second conduit 14 could be surgically implanted in a ureter 18 which leads to bladder 16. Elements 8 and 14 would typically be catheters.

Figure 2:
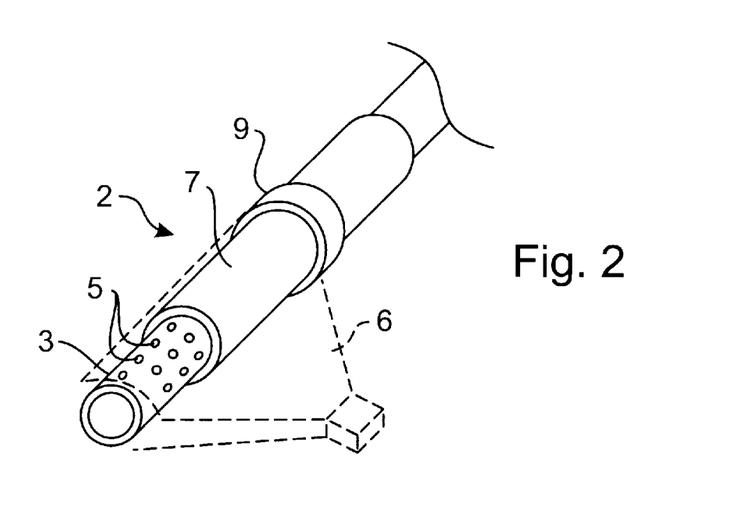
FIG. 2 is a perspective view of a portion of the device shown in FIG. 1.

Graft 2 is shown in greater detail in FIG. 2 and is composed of a tubular member 3 which is grafted in a conventional manner to each part 4 of a blood vessel. Over a portion of the length of graft 3 there are provided a plurality of perforations, pores, or channels 5 permitting the flow of fluid through graft 3. Graft 3 is surrounded by a membrane 7 of a material which permits ultrafiltration, i.e. permits the passage of plasma, fluids and low to medium molecular weight substances, but blocks the flow of blood cells and protein. Membrane 7 is secured in place, along with funnel-shaped member 6, by any suitable means, such as two annular clamps 9, one of which is shown in FIG. 2. Member 6 is shown in broken lines to simplify the illustration.

The blood vessel in which graft 2 is interposed can be an artery, a vein, or any other vasculature which provides adequate blood flows. An artery will enhance hydraulic fluid removal, because it conducts blood at higher pressures, while a vein, which conducts blood at lower pressures, may permit greater fluid removal when negative pressure is applied by pump 10 across membrane 7.

In order to prevent, or at least minimize, clotting at the site of graft 2, tubular member 3 may be made of a material which resists clotting such as GoreTeX™, polytetraflouroethelene (PTFE), silicone or a similar biocompatible material. These materials are commonly used for vasculature in the human body. These can be made hydrophobic in order to aid in the passage of fluid from the blood vessel, through membrane 7 into conduit 8.

Pores, or channels, 5 can be cut in tubular member 3 by an excimer laser or by other means known in the art and are formed only in the region of member 3 which is enclosed by clamps 9. Pores 5 can be circular, as shown, or can have any other form, such as rectangular or elliptical.

Membrane 7 can be made of a hollow fiber dialyzer material of the type employed in hemodialysis and hemofiltration to remove toxins and/ or fluid. Such material may include, but is not limited to, cellulose acetate, cupramonium, or polysulfone. These materials vary in biocompatability.

Standard dialysis membranes have the pore sizes suitable for the present invention. The standard method of designing membranes with the proper pore size and quantity is to manufacture the fibers mixed with additional solutes and chemicals. After the initial stage of manufacturing, the fibers are rinsed with a solution which removes many of the solutes in the fiber walls leaving pores the size of these solutes and the quantity is dependent upon the quantity of the solutes used in the first stage of the manufacturing process. This manufacturing process is known to those in this field. Membrane 7 can easily be manufactured in a similar manner.

The required ultrafiltration rate of 0–15 ml/min (for ultrafiltration) can be easily obtained given the dialyzer characteristics of these membrane materials. Long term internal use of the device would be enhanced by the use of a membrane material having a reduced tendency to induce clot formation. While the required ultrafiltration rates for fluid removal should range between 0–15 ml/min, the device can be modified to provide ultrafiltration rates of up to 50 ml/min if necessary.

One possible site for the device is in the pelvis using the iliac artery as the blood access. The flow of blood through the iliac artery is as high as 5% of cardiac output. Cardiac output is normally 5 liters/min, which would imply a blood flow of 250 ml/min through the iliac artery. Hematocrit for healthy individuals is 45%, so the plasma flow through the iliac artery vessel is 55%, resulting in a plasma flow of 140 ml/min for an arterial blood flow rate of 250 ml/min. Thus, the removal of 15 ml/min through membrane 7 would involve removal of approximately 10% of the total plasma fluid flow. Most dialysis patients have a lower hematocrit, resulting in a higher percentage of plasma flow and therefore the need to remove a smaller percentage of the plasma fluid.

The key location should be in the pelvis, and subcutaneous placement is possible if the femoral artery and femoral vein are used. The connection to the ureter and/or bladder would require surgical implantation. By placing the device subcutaneously, it will facilitate the palpation of the location, enhance the telemetry capabilities including recharging subcutaneously, provide simple access to the device under a local anesthetic. In addition, the injection ports can be easily located. Subcutaneous insertion also places the pump anterior to the ureter and/or bladder thereby enhancing flow to the ureter and/or bladder by the use of gravity in addition to the pump system.

The negative pressure caused by pump 10 at its inlet is set to remove only the required amount of fluid so as not to drag blood cells against the graft. In addition, plasma fluid will filter through the membrane simply by the hydraulic forces of the blood flow through the vascular access segment. Pump 10 will therefore act as a regulator so only the desired fluid removal is achieved. The pump is essential to the implantable device because without control of the ultrafiltration rate, the patients may become hypotensive.

Complications which may arise include fibrin clotting of the fluid channels. Clotting of graft 2, in general, is not a problem because the flow of the blood through the graft is sufficient to prevent clotting. Grafts are currently used for longterm vascular use. To prevent fibrin from filling pores 5 in tubular member 3, pump 10 may be programmed to backfilter or reinfuse plasma at a specified rate, e.g. $\frac{1}{10}$ the rate of ultrafiltration. For example, if 3 ml/min are required to be removed from the blood flow to obtain correct dry weight for a patient, fluid could be removed at a rate of 3.3 ml/min for ten minutes, followed by reversal of pump 10 to backfilter fluid at a rate of 3 ml/min for one minute in order to clear any material, such as fibrin, fibrinogen, protein, etc., which may be starting to fill pores 5. The duration of these periods can be determined clinically and can be adjusted by telemetry.

After ultrafiltrate passes through membrane 7, it passes through a conduit, or catheter, 8 to pump 10. Conduit 8, as well as catheter 14, can be made of any of the materials which are suitable for tubular member 3. Conduits 8 and 14 can be secured to the inlet and outlet of pump 10 by any suitable means, such as clamps or gaskets of appropriate biocompatible material.

Pump 10 may have a housing made of stainless steel or other biocompatible material and the housing will enclose the pumping components, pump tubing segments, telemetry system, and a battery/power supply. The dimensions of the housing should be small enough for permanent implantation in the desired location, e.g. placement in the pelvis, without causing discomfort to the patient or structural trauma.

Pump 10 can be constituted by any one of a number of commercially available products, such as the model MMT-2001 implantable pump marketed by MiniMed Technologies of Sylmar, Calif. The interior pump tubing segment is made of a durable material which can resist long-term pump pressures. The total volume of the tubing segment will be between 0.1 to 10 cc, dependent on patient fluid removal requirements and optimal rotation of the pump heads. The shape of this segment could be horseshoe or round or similar in order to effectively pump the ultrafiltrate through the device. The interior pump segment should be fastened into the housing unit in order to prevent disconnection.

Preferably, pump 10 is a rotary pump, however other pumps, such as membrane, piezoelectric, pressure, etc., producing the required action may be used.

The voltage demands and output torque should be designed to: 1) produce a relative negative pressure in the vascular access conduit 8 for filtration or for delivery of the required fluid which may pass through membrane 7 by hydraulic forces; 2) produce the desired effects of pumping the ultrafiltrate at the desired flow rates; 3) optimize battery life; and 4) pose minimal risk of electrical shock to the patient. These objectives may be achieved in accordance with principles known in the art.

The pump should be constructed to meet the following requirements: 1) The pump life must be as long as possible without complications, the above-cited MiniMed pump having a battery life of 3 years; 2) the pump segment should have a number of heads sufficient to continuously prevent undesired backflow as the pump heads rotate ,this being dependent on the shape of the pump tubing segment; 3) The pump must be controllable and programmable by telemetry in order to allow variation of the ultrafiltration rates and to program the rates throughout the day, e.g. to reduce the ultrafiltration rate, or terminate ultrafiltration, at night since the patient does not drink while sleeping; and 4) pump rotation should be reversible in order to clear the vascular compartment from blockages as previously mentioned. A reversible pump can be constructed by using an available reversible motor as the pump motor. One such reversible motor is marketed by MicroMo Electronics, Inc. of Clearwater, Fla., under the designation DC MicroMotors Series 1212.

Conduit 8 is connected to pump 10 via an inlet coupling having a static injection port 22 and conduit 14 is connected to pump 10 via an outlet coupling having a similar static injection port 24. Ports 22 and 24 may be silicone ports which allow for injection of antibiotics, anticoagulants, or clot dissolving agents (such as TPA or the like) to break up clots or fibrin deposits which may block the ultrafiltration membrane. The pump should be capable of running in reverse if the desire is to clear the membrane channels. Antibiotics may be necessary if an infection occurs anywhere along the system's path. These antibiotics can be administered through said injection ports 22 and 24.

The oral administration of a clot preventing drug such as crystalline warfarin sodium can be prescribed in order to reduce the risk of clotting. Crystalline warfarin sodium is presently prescribed for mitral valve and other artificial implants to reduce the risk of clotting. This should be mentioned to add to the credibility of the device.

Conduit 14 may be designed for ease of fluid movement from the pump unit to the ureter or bladder. This conduit will be as short as possible without increasing the risk of disconnection from either the housing unit or the ureter, or bladder, while still permitting uninhibited movement of the patient's body. If possible, conduit 14 should leave the housing of pump 10 at a position superior and anterior to the ureter connection. This will aid flow of the ultrafiltrate when the patient is standing or lying on their back. The connection to the ureter, or bladder, must be tight to prevent possible leaking into the surrounding areas. A one-way valve 25 may be used at the outlet coupling of pump 10 to prevent back flow during peristaltic flow. A bellows type reservoir may be incorporated to permit backflow without collapsing the conduit, when the pump is in reverse.

A telemetry and control system 26 is included to both control the operation of pump 10 and retrieve information about the device. System 26 preferably includes a programmed microprocessor controlled unit having condition measurement and data storage capabilities. This unit will be connected, via inputs 28 and/or via inputs connected within pump 10, to receive data signals indicating the flow rate and cumulative quantity of fluid drawn through membrane 7, the charge level of the pump power supply battery, the pump inlet and outlet pressures, the conductivity of ultrafiltrate, and protein concentration or hematocrit of the blood for regulation of fluid removal. The unit may additionally be programmed to perform a clock function in order to allow pump operation to be varied at different times of the day and to allow various parameters to be controlled and/or monitored via telemetry. The unit may include further components, known per se, for recharging the pump battery transdernially.

The parameters that may be controlled and/or monitored via telemetry include pump speed settings and times to allow different rates of removal during different time periods over the course of each day, and setting or resetting the time of day by telemetry when necessary, total fluid removed per day and during each time period.

Operation of the device can be diagnosed by comparing pump inlet and outlet pressures with acceptable limit values to identify possible disconnections or blockages, and calculating remaining battery life and an alarm may be produced when battery life is low. The measured parameters can also be used to diagnose pump complications.

In addition the fluid removal rate can be controlled on the basis of measurements of conductivity, and hematocrit or protein concentrations.

Transonic Systems, Inc. makes a doppler flow meter which has recently entered the dialysis market. This sensor works by the ultrasound properties of protein bound to red blood cells. In addition, this device can be modified to determine access recirculation (percentage of blood that leaves the venous line and returns back into the arterial line during hemodialysis). The method of determining access recirculation is to dilute the blood protein with a bolus saline injection and measuring the change in magnitude of the doppler signal. Protein has been shown to remain constant in the extracorporeal space and the concentration is changed primarily by dilution. This technology can be incorporated into the vascular access part of the ultrafiltration (Uf) device and a relative protein concentration can be determined. This can be calibrated by concurrent lab values of protein concentrations and then the value can be passed to the device by telemetry. It is not necessary to determine an absolute concentration of the protein, but a relative concentration. The protein concentration will decline as fluids are consumed and stored in the vascular space. If the device is calibrated to a known value, the implantable device can control the rate of fluid removal in order to 1) keep the protein concentration constant or 2) keep the change in protein concentration equal to zero. Incorporating this device into an implantable device should not be difficult since it only requires two small transducers on each side of the vascular access. Direct blood contact is not required.

The second method for determining changes in blood volume are an optical hematocrit monitor. This will be more difficult to implant since it measures the absorptive and refractive properties of blood. This requires direct view of the blood. This could be worked into the vascular access device, however it may be difficult to perform. In-Line Diagnostics Inc. manufactures a continuous read optical hematocrit monitor for hemodialysis. This device is called a Crit-line Monitor. The Hemoscan monitor, by Hospal, determines hematocrit in a similar manner but uses an infrared light and absorption properties. Flematocrit should be mentioned as a possible control mechanism which can be used as an implantable device or externally as a home test method of volume status.

The third determination of blood volume is the conductivity measurement of sodium in the vascular space. The quantity of sodium in the body tends to remain constant, therefore the concentration is dependent on the volume status of the patient. This can be measured with a simple device used in many aspects of renal replacement therapy. This device works by using two magnetic cores. One core produces a magnetic field across the blood vessel while the second core senses the inductive reactance of the blood. COBE Renal Care (part of Gambro HealthCare) has a monitor which measures the differential conductivity between the venous and arterial lines to measure recirculation rates, however this specific device is not implantable. This device measures recirculation by injecting a hypertonic solution into the blood lines. A positive change can be measured as compared to the baseline conductivity. The measurement of a hypertonic solution will not be necessary for the Uf device because we are only interested in the change over time of the conductivity or the lack of change in conductivity implying the fluids are removed as consumed. This value can also be calibrated at monthly chemistries and the value can be sent via telemetry.

The conductivity sensor is ideal for a feed back loop when used with the peritoneal hemodiafiltration method, to be described. Since a slightly hyper sodium (hypertonic) solution will be infused into the peritoneal cavity, the sodium concentration should increase in the vascular space. The concentration of sodium (Na) in this vascular space should reflect both the rate of sodium absorption from the peritoneal cavity and the rate of ultrafiltration with the Uf device.

$Na_t$=total $Na_{t-1}$+Na absorbed from the peritoneal cavity −Na removed by Uf device, where $Na_t$ is the sodium concentration measured at a time t, and $Na_{t-1}$ is the sodium concentration measured at a previous time t-1. If we measure the Na concentration of the fluid removed by the Uf device, it should reflect the Na concentration in the vascular space. Since we are infusing a hyper saline solution in the peritoneal cavity, the plasma Na concentration should increase as the filter removes the more dilute Na plasma fluid and this is replaced by the hyper sodium solution of the peritoneal dialysis fluid. A feed back loop can measure the ultrafiltrate (plasma fluid removed by Uf device) Na concentration and change the rate of removal dependent on the changes in the vascular space. If the peritoneal fluid is entering the vascular space faster than the Uf device is removing the fluid, the Na concentration will increase faster than expected. If the UF device is removing fluid faster than the peritoneal fluid is absorbed into the vascular system then the sodium concentration will change only slightly.

If a patient has 10 liters of extracorporeal space and a concentration of 140 meq/dl then they would have a total of 135 meq/dl*100 dl=13500 meq. If the peritoneal solution has Na of 140 meq/dl and a total of 2 liters (140 meq/dl*20 dl=2800 meq.) If no fluid were to be removed from the vascular space and all of the peritoneal fluid becomes absorbed into the body, the new concentration would be ((13500+2800)/120)meq/dl=136 meq/dl. This appears to be a small change, however with the hemodiafiltration method the quantity of fluid infused is not 2 liters but is 10 liters per day. At these quantities, if the equilibrium equation is shifted to one side or the other, detection will be possible. Again we are looking for relative amounts and not absolute Na concentrations. In addition, for those patients with no residual renal function, the Na concentration of the ultrafiltrate is the same as the fluid they excrete from their bladder (urine). They can take a small aliquot of this urine solution and determine the Na concentration and via telemetry calibrate the Uf device. The device will then increase or decrease the removal rate as necessary in order to maintain euvolemia.

Devices according to the invention may have several uses in addition to ultrafiltration in renal failure. They may be used for incontinence if the neck of the bladder is surgically closed and the pump is used to pump urine from the bladder around the closure to be void. The catheters can be shortened, the pump speed can be enhanced and the tubing diameter can be larger. A radio frequency or other telemetry device can be used to start and stop the pump as needed.

In further accordance with the present invention, ultrafiltration to remove waste and other fluids from the circulatory system can be supplemented by a novel peritoneal dialysis (PD) procedure which comprises infusion of controlled quantities of a non-osmotic solution into the peritoneal cavity for uptake by the circulatory system. This can be done in conjunction with use of the implantable ultrafiltration device described above or in conjunction with any other hemofiltration system employed in the treatment of renal failure. This form of dialysis can be used for chronic renal replacement therapy or for the treatment of acute renal failure.

In the peritoneal dialysis procedure according to the invention, a peritoneal dialysate solution without the osmotic agents (i.e. glucose, dextrose, dextran, etc.) is administered. When this is done in conjunction with a hemofiltration system, it is possible to effect a dialysis which is superior to current peritoneal dialysis methods. The hemofiltration system will be modified to increase fluid removal. At a rate of 10 ml/min (adequate dialysis clearance) this would yield 600 ml/hr fluid removal.

A peritoneal dialysis patient normally infuses two liters of fluid, four times a day, and consumes an additional liter or more of fluid. The total fluid intake is, therefore, 9 liters per day (2 liters×4 exchanges+1 liter fluid consumed). Large patients tend to consume as much as 3 liters per day and can take 2.5 liters of dialysate in their peritoneum, yielding total fluid intake of 13 liters per day or more. The goal of the peritoneal non-osmotic fluid is to replenish all of the electrolytes and quantity of fluids removed by the ultrafiltration device. This would yield average clearance values of 10 ml/min in larger patients and therefore adequate dialysis. Overall clearance values would be improved, dialysate exchange times would be reduced, and complications due to the large glucose concentrations of currently used dialysate would be eliminated (no glucose or dextrose would be required). The patient would have better control of their dialysis prescription and could improve clearances as necessary. The programmability of the device will need to be slightly modified in order to remove at the same rate as absorption from the peritoneal cavity into the vascular system. Measurement of protein, hematocrit or conductance of ultrafiltrate will improve control of filtration and dialysis and the measurement results can be used in a closed loop control system to increase the removal rate or to slow down the removal rate.

The peritoneal fluid would be similar to dialysate used for hemodialysis.

Acute renal failure requires immediate renal replacement therapy in order to control acid base balance and volume overload. Many of these patients have multiple organ complications and therefore need a less abrasive treatment than that of conventional hemodialysis. Two currently used methods of renal replacement therapy for acute renal failure are continuous arterio-venous hemofiltration (or hemodiafiltration) (CAVH) and continuous veno-venous hemofiltration (or hemodiafiltration)(CVVH). Hemodiafiltration consists of reinfusion of a sterile solution. These modalities may be enhanced with the use of counter current flow of dialysate in order to improve the diffusion of urea. The advantage of these therapies is that they are less stressful on the body and provide continuous treatment as opposed to 3–4 hour hemodialysis sessions.

Conventional hemodiafiltration modalities as described above are performed by obtaining vascular access by catheterization of a major vessel and allowing the blood to flow through an external hemofilter in order to remove the toxins and excess fluids. Excess fluids can be removed at rates approaching 50 ml/min or greater. At this rate the patients will become hypotensive in a short period of time, unless fluids are returned to the system. This is usually performed by catheterization of another vessel with a saline/dialysate drip or saline/dialysate fluid substitution directly into the return (venous) line from the hemofilter. Fluid substitution directly into the blood volume as with both of these therapies opens the patient to significant risk for infection.

Peritoneal dialysis has also been used for the treatment of acute renal failure. A catheter is inserted into the peritoneal cavity and dialysate is infused. This fluid has high osmotic properties in order to remove excess fluid. Two liters of dialysate can be infused into the peritoneal cavity and allowed to equilibrate. After six hours, the effluent is drained and a fresh dialysate is infused. Except for exchanges, the peritoneal cavity is always filled with dialysate, thereby providing continuous dialysis. In some instances, a patient may be connected to a machine which automatically pulls the effluent out and reinfuses fresh dialysate. Such a device is called a cycler. This device eliminates the number of connections and disconnections of PD therapy. The complications with PD therapy relate to the slow clearance characteristics of PD and the high glucose solutions used in each exchange.

The PD procedure according to the present invention, when used to treat acute renal failure, utilizes a non-osmotic solution which is infused into the peritoneal cavity and a hemofiltration method to pull fluid and solutes out of the blood. The hemofiltration method can be performed by a device such as the implantable ultrafiltration device according to the present invention or an external hemofilter such as used in conventional CAVH or CVVH.

The advantage of the procedure according to the present invention is that the peritoneal cavity is used as the site for replacement fluids. This has the advantage that it uses the peritoneal membrane to infuse the fluid into the body. The peritoneal membrane acts as an infusion filter to more naturally replace the fluids removed. In addition, removal can be improved since direct arterial or venous infusion dilutes the central blood compartment, thereby decreasing removal whereas the peritoneal membrane infuses the fluid over a wide capillary bed, reducing direct dilution of the blood.

Treatment of acute renal failure using a non-osmotic peritoneal solution in conjunction with a method of hemofiltration may improve patient outcomes by carefully restoring acid base balance, gently clearing the toxins from the body and continuously removing excess fluids. This method may be less traumatic to the patient, thereby improving the patient's chances for recovery. Renal recovery may also be enhanced.

In the case of chronic renal failure, approximately 25% of the dialysis patients in the United States are on PD. Here again, this is conventionally performed by infusing an osmotic dialysate solution through a catheter into the peritoneal cavity. Toxins such as urea and creatinine and excess fluid are removed from the blood through capillary beds which interface with the fluid in the peritoneal cavity. After approximately 6 hours, when the blood and dialysate have equilibrated, the dialysate fluid (effluent) is drained and a fresh dialysate solution is infused. Usually, two (2) liters of dialysate fluid are infused into the peritoneal cavity and allowed to equilibrate with the blood. Four to five exchanges are performed every day, seven days a week. A long dwell is performed at night as the patient sleeps. PD clearance (4–8 ml/min) is less efficient than hemodialysis clearance (150–450 ml/min). However, since PD is continuously performed, adequate dialysis is possible. Prescription usually calls for a weekly Kt/V for urea nitrogen of 1.7. This implies that the body volume (space where urea nitrogen equilibrates) needs to be cleared 1.7 times/week. A 70 kg patient with fluid space of 58% of body weight requires 69 liters of clearance per week. If each PD exchange is assumed to equilibrate, then this patient would require 5 exchanges of 2 liters each (5 exchanges×2 liters×7 days=70 liters per week). Another alternative is to increase the volume of each exchange. For example, the same treatment may be possible with 4 exchanges per day of 2.5 liters each (4 exchanges×2.5 liters×7 days=70 liters per week). The prescription is dependent on each patient's peritoneum's characteristics for movement of solutes and fluid and each patient's peritoneal cavity's capacity to hold fluid. Smaller patients may not be able to hold more than 2 liters in their peritoneal cavity, but may also require fewer liters of exchange in order to receive adequate dialysis.

The dialysate fluid used for conventional PD is a combination of the electrolytes the body requires and a glucose/dextrose type osmotic solution used to increase osmotic forces and permit fluid removal from the blood volume into the peritoneal cavity. Recently the effect of the glucose/dextrose solutions on the body has been questioned. Continuous elevated insulin levels have been reported in PD patients. In addition, the long term effects of hyperinsulinemia is known to cause vascular damage.

According to the present invention, treatment of chronic renal failure involves fluid removal from the circulatory system, the removed fluid being termed ultrafiltrate, preferably with the novel inplantable ultrafiltration device described earlier herein, and periodically partially or fully filling the peritoneal cavity with a modified non-osmotic solution (no glucose or dextrose or the like). This therapy is termed continuous ambulatory hemodiafiltration and thus consists of the removal of plasma water (but not protein) and the concurrent infusion of an electrolyte fluid into the peritoneal cavity. The electrolyte solution will provide the patient with the proper blood and body requirements of the electrolytes and proper acid base regulation.

The theory of continuous ambulatory hemodiafiltration is to remove toxins from the circulatory system by ultrafiltration of plasma water (not removing the proteins) from the blood compartment and concurrently reinfusing electrolytes and fluid through the peritoneal membrane in order to maintain proper pH and electrolyte concentrations. The amount of ultrafiltration and reinfusion required for the adequate treatment of renal failure depends on the patient size but can be prescribed similar to peritoneal dialysis, volume required=1.7×body volume.

The implantable ultrafiltration device according to the present invention can be modified to enhance clearance relative to its intended performance as an excess fluid removal system. This permits increased fluid removal as necessary. The determinant factor will therefore be the rate of absorption of the electrolyte fluid from the peritoneal cavity into the blood volume. The faster the absorption, the faster the ultrafiltration pump should operate and the less time required for dialysis.

Since the absorption of fluids from the peritoneal cavity will be dependent upon the oncotic forces of the protein in the extracorporeal volume, the rate of absorption will be partially dependent on the rate of fluid removal. As fluid is removed more slowly, the oncotic forces decrease because of dilution. As the oncotic forces decrease, fluid is absorbed by the extracorporeal blood volume more slowly. This system works in reverse as well. The faster the fluid removal from the blood volume, the greater the protein concentration and the greater the oncotic pressure, and the greater the oncotic pressure, the faster the absorption of fluid from the peritoneal cavity. This permits some self regulation of fluid removal and absorption.

The rate of absorption can be determined clinically by measuring concentrations of a solute which is not easily transferred across the peritoneal membrane. The concentration can be plotted over time and a rate can then be determined. This will enhance prescription.

The elimination of the ostnotic agent fiom most, if not all, of the exchanges will reduce the complications associated with a glucose or dextrose type solution. These complications include elevated insulin levels and possibly increased peritonitis rates. Peritonitis rates may improve with continuous ambulatory hemodiafiltration because of the elimination of the sugar solutions which tend to be ideal environments for bacteria and other organisms known to cause peritonitis.

According to one alternative mode of implantation, graft 2 may be implanted as a bypass around a portion of an artery or vein, in which case each end of graft 2 would be implanted in the wall of the artery or vein.

Figure 3:
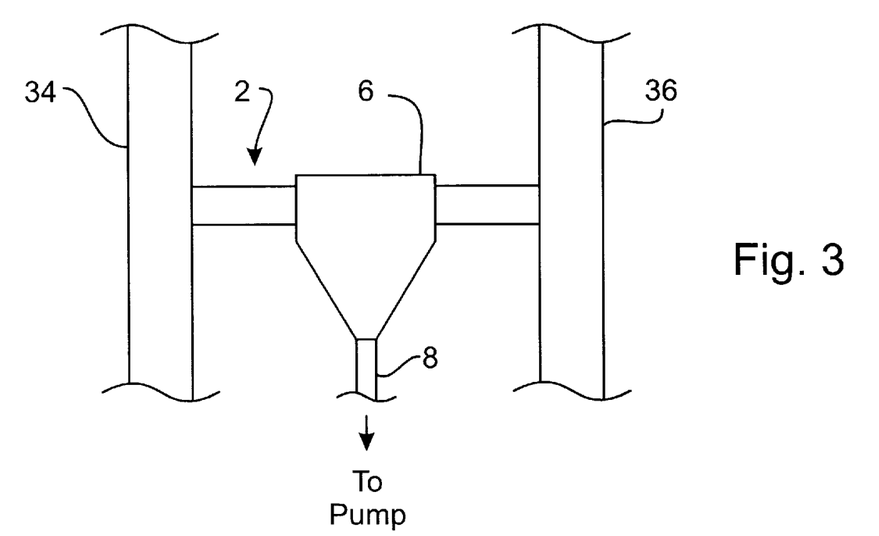
FIG. 3 is a simplified pictorial view showing an alternative implantation scheme for a device according to the invention.

The invention may also be practiced by implanting tubular graft 2 between two blood vessels 34 and 36, as shown in FIG. 3. Either vessel 34, 36 may be an artery or a vein. If the filter provided in tubular graft 2 is constructed to require blood flow in a particular direction through graft 2, and if one vessel is an artery and the other a vein, graft 2 should be installed so that the appropriate direction of blood flow therethrough is from the artery to the vein.

Figure 4:
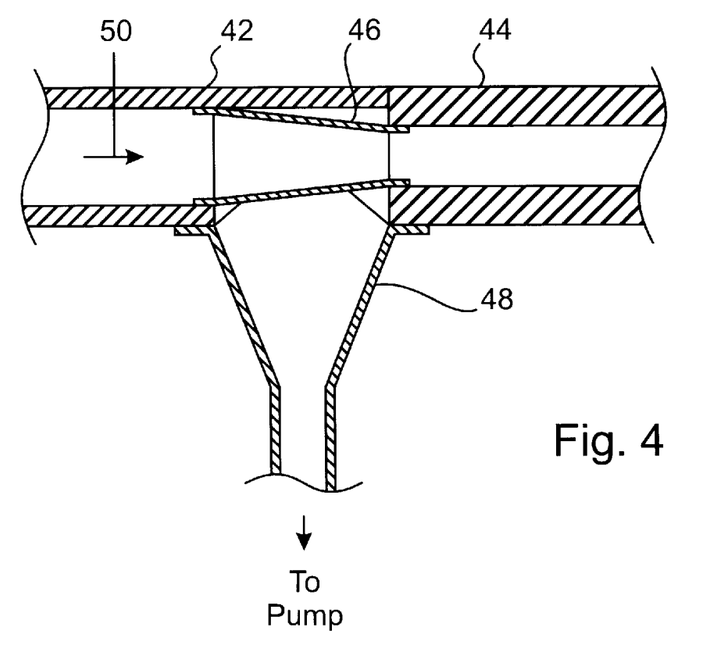
FIG. 4 is a cross-sectional view showing another embodiment of a portion of a device according to the invention.

Another embodiment of a tubular graft according to the invention is illustrated in the cross-sectional view of FIG. 4. In this embodiment, the graft is composed of two conduits 42, 44 joined together at their ends, conduit 42 having a larger inner diameter than conduit 44. A frustoconic filter element 46 is installed at the end of conduit 42, the large diameter end of element 46 being secured to the inner wall of conduit 42 and the small diameter end of element 46 being secured to the inner wall of conduit 44. Within the end region of conduit 42 there is thus provided a space for receiving ultrafiltrate. This ultrafiltrate is permitted to pass through an opening in the wall of conduit 42 into a funnel-shaped member 48, from which it will flow to the associated pump.

Filter element 46 is preferably made porous around its entire circumference and may either be self-supporting or provided with a suitable perforated or porous supporting member.

The graft shown in FIG. 4 will be installed in a manner to support blood flow in the direction of arrow 50. Because of the tapered form of element 46, blood flowing therethrough experiences a pressure increase which will promote the passage of components having low to medium molecular weights through filter element 46.

The embodiment shown in FIG. 4 can be implanted in accordance with any of the techniques described above and can be inserted into the desired blood vessels by anastomosis.

The increase in pressure experienced by blood as it passes through frustoconic element 46 will provide enhanced removal of ultrafiltrate. In addition, it will result in an increase in the force with which blood cells and protein are propelled along the length of filter element 46, thereby reducing the danger of development of obstructions.

Tubular graft 2 can also be given a curved form, especially in the region of filter element 46. Such a curved form has been found to help prevent obstruction of the filter pores.

The device and method according to the present invention are intended to enhance treatment delivered to the patient, improve patient control of dialysis delivered, improve the quality of life of the patient, improve patient fluid management and excess fluid control and decrease many of the complications associated with conventional peritoneal dialysis.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed:

1. An implantable ultriltration device for removing fluid from a patient experiencing renal failure, said device comprising:

regulator means having an inlet, an outlet and means for regulating the flow of fluid from the inlet to the outlet;

first means for forming a first fluid flow path between the patient's vascular system and said regulator means inlet;

a filter interposed in the first fluid flow path, said filter being permeable to water and substantially impermeable to blood cells and protein; and second means for forming a second fluid flow path between said regulator means outlet and the patient's bladder, wherein said regulator means, said first means, said second means and said filter are all constructed to be surgically implanted in the patient's body.

2. The device of claim 1 wherein said first means comprise a tubular graft permanently implantable to form a section of a vascular system.

3. The device of claim 2 wherein said filter is a hollow fiber membrane.

4. The device of claim 3 wherein said filter is permeable to low to medium molecular weight solutes, plasma and water.

5. The device of claim 1 further comprising means for controlling said regulator means in response to a measured parameter representative of the fluid content of the vascular system.

6. The device of claim 1 further comprising means for permitting fluid to flow through said second flow path in only one direction from said regulator means.

7. The device of claim 1 wherein said first means and said filter are constructed to produce a fluid flow through said filter at a finite rate not greater than 15 ml/min.

8. The device of claim 1 wherein said filter has a frusto-conic form.

9. The device of claim 1 wherein the fluids to be removed contain low to medium molecular weight solutes.

10. The device defined in claim 1, said implanted by:

implanting the regulator means and the second means in the patient's pelvic region;

inserting the first means into vasculature in the pelvic region with the filter disposed outside the vasculature; and implanting an outlet end of said second means in a component of the patient's urinary system.

11. The device according to claim 10 wherein the vasculature is an artery.

12. The device according to claim 10 wherein the vasculature is a vein.

13. The device according to claim 10 wherein the vasculature is an artery and vein.

14. The device according to claim 10 wherein the component is the ureter.

15. The device according to claim 10 wherein the component is the bladder.

16. The device according to claim 1 used for removing excess fluids from the blood of a patient experiencing renal failure by connecting the first means in the vascular system of the patient and implanting the second means in the patient's bladder or ureter; and operating the regulator means to regulate the flow through the filter at a controlled rate in order to maintain the fluid volume in the patient's body at a selected value.

17. The device according to claim 16, which is used together with periodically infusing a quantity of a peritoneal solution which is substantially free of osmotic agents into the peritoneal cavity of the patient, and allowing the solution to be absorbed into the patient's circulatory system.

18. The device of claim 1 wherein said regulator means comprise a pump.

19. The device of claim 1 wherein said filter comprises a body of material which extends across the first fluid flow path and is permeable to water and substantially impermeable to blood cells and protein.

20. A method of treating a patient experiencing renal failure, comprising introducing a quantity of a peritoneal solution which is substantially free of osmotic agents directly into the peritoneal cavity of the patient, and allowing the solution to be absorbed into the patient's blood and removing absorbed fluid by a means for filtration.

* * * * *